(12) United States Patent
Gribkov et al.

(10) Patent No.: US 9,878,970 B1
(45) Date of Patent: Jan. 30, 2018

(54) PROCESS FOR THE PREPARATION OF BENZONORBORNENES

(71) Applicant: Syngenta Crop Protection, LLC, Greensboro, NC (US)

(72) Inventors: Denis Gribkov, Munchwilen (CH); Bjorn Antelmann, Breitenloh (CH); Fanny Bois, Basel (CH); Harald Walter, Munchwilen (CH); Alain De Mesmaeker, Munchwilen (CH)

(73) Assignee: Syngenta Crop Protection, LLC, Greensboro, NC (US)

( * ) Notice: Subject to any disclaimer, the term of this patent is extended or adjusted under 35 U.S.C. 154(b) by 0 days.

(21) Appl. No.: 15/717,327

(22) Filed: Sep. 27, 2017

Related U.S. Application Data

(62) Division of application No. 14/603,857, filed on Jan. 23, 2015, now Pat. No. 9,796,646, which is a division of application No. 13/126,380, filed as application No. PCT/EP2009/062525 on Sep. 28, 2009, now Pat. No. 9,115,043.

(30) Foreign Application Priority Data

Oct. 27, 2008 (EP) .................................... 08018721
May 28, 2009 (EP) .................................... 09161388

(51) Int. Cl.

| | | |
|---|---|---|
| *C07C 22/02* | (2006.01) | |
| *C07C 22/04* | (2006.01) | |
| *C07C 205/06* | (2006.01) | |
| *C07C 205/11* | (2006.01) | |
| *C07C 205/12* | (2006.01) | |
| *C07C 17/32* | (2006.01) | |
| *C07C 17/266* | (2006.01) | |
| *C07C 209/36* | (2006.01) | |
| *C07C 17/23* | (2006.01) | |
| *C07C 17/26* | (2006.01) | |
| *C07C 201/12* | (2006.01) | |

(52) U.S. Cl.
CPC ............ *C07C 17/32* (2013.01); *C07C 17/23* (2013.01); *C07C 17/26* (2013.01); *C07C 17/266* (2013.01); *C07C 22/02* (2013.01); *C07C 22/04* (2013.01); *C07C 201/12* (2013.01); *C07C 205/06* (2013.01); *C07C 205/11* (2013.01); *C07C 205/12* (2013.01); *C07C 209/365* (2013.01); *C07C 2601/10* (2017.05); *C07C 2603/66* (2017.05)

(58) Field of Classification Search
CPC ..... C07C 22/04; C07C 22/02; C07C 205/206; C07C 205/11; C07C 205/12; C07C 2601/10; C07C 2603/66
See application file for complete search history.

(56) References Cited

U.S. PATENT DOCUMENTS

2008/0227835 A1* 9/2008 Tobler .................. A01N 43/32
514/365

FOREIGN PATENT DOCUMENTS

| WO | WO-2007031323 A1 * | 3/2007 | ........... C07D 231/14 |
| WO | 2007/048556 | 5/2007 | |
| WO | 2007/048556 A1 | 5/2007 | |
| WO | 2007/068417 A2 | 6/2007 | |

OTHER PUBLICATIONS

Olsson, Thomas & al.: "6-Substituted Fulvenes from Tri8uoromethylcyclopentadiene" in: Acta Chemica Scaninavica B 32 (1978), pp. 298-296.

Moberg et al—6-Halogenofulvenes and Allylcyclopentadiene from Nickelocene—Journal of Organometallic Chemistry 49 1973 (p. 243-248).

International Search Report for International Patent Application No. PCT/EP2009/062525 dated Jan. 12, 2010.

BO Patent Application No. SP-327-2009 Substantive Examination Report/Office Action (Letter from foreign agent dated May 9, 2014) and Instructions to foreign agent to prepare response to Office Action dated Jun. 24, 2014.

* cited by examiner

*Primary Examiner* — Medhanit W Bahta
(74) *Attorney, Agent, or Firm* — James Cueva

(57) ABSTRACT

The present invention relates to a novel a process for the preparation of 9-dichloromethylene-1,2,3,4-tetrahydro-1,4-methano-naphthalen-5-ylamine which process comprises a) reacting cyclopentadiene in the presence of a radical initiator and CXCl3, wherein X is chloro or bromo, to a compound of formula I1, or aa) reacting cyclopentadiene with CXCl3, wherein X is chloro, in the presence of a metal catalyst to a compound of formula I1, wherein X is chloro, b) reacting the compound of formula I1 with a base in the presence of an appropriate solvent to the compound of formula III, c) and converting the compound of formula III in the presence of 1,2-dehydro-6-nitrobenzene to the compound of formula IV, and d) hydrogenating the compound of formula IV in the presence of a metal catalyst.

1 Claim, No Drawings

PROCESS FOR THE PREPARATION OF BENZONORBORNENES

RELATED APPLICATION INFORMATION

This application is a divisional of U.S. patent application Ser. No. 14/603,857, filed Jan. 23, 2015 which is a divisional of U.S. patent application Ser. No. 13/126,380 filed Apr. 27, 2011, now patented as U.S. Pat. No. 9,115,043 issued Aug. 25, 2015, which was a 371 application of International Application No. PCT/EP2009/062525, filed Sep. 28, 2009, which claims priority to EP Patent Application 08018721.4, filed Oct. 27, 2008, and EP Patent Application No. 09161388.5 filed May 28, 2009, the contents of which are incorporated herein by reference herein.

The present invention relates to the preparation of 9-dichloromethylene-1,2,3,4-tetrahydro-1,4-methano-naphthalen-5-ylamine.

The compound 9-dichloromethylene-1,2,3,4-tetrahydro-1,4-methano-naphthalen-5-ylamine is a valuable intermediate for the preparation of benzonorbornene fungicides, as described for example in WO 2007/048556.

It is known from WO 2007/048556 to prepare 9-dichloromethylene-1,2,3,4-tetrahydro-1,4-methano-naphthalen-5-ylamine by a) reacting the compound of formula A

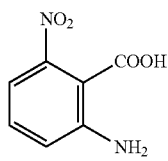

(A)

in the presence of an alkyl nitrite
with a compound of formula B

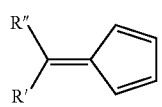

(B)

wherein R' and R" are e.g. $C_1$-$C_4$alkyl, to a compound of formula C

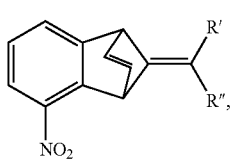

(C)

b) hydrogenating the compound of formula C in the presence of a suitable metal catalyst to a compound of formula D

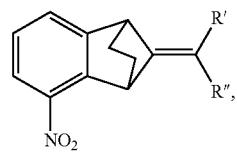

(D)

c) ozonising the compound of formula D with subsequent treatment with a reducing agent to a compound of formula E

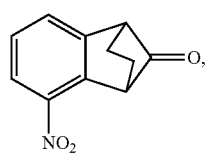

(E)

d) reacting the compound of formula E triphenylphosphine/carbon tetrachloride to 2,9-dichloromethylidene-5-nitro-benzonorbornene of formula F

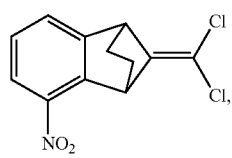

(F)

and e) hydrogenating the compound of formula F in the presence of a metal catalyst to 9-dichloromethylene-1,2,3,4-tetrahydro-1,4-methano-naphthalen-5-ylamine.

A disadvantage of this prior art process is the large number of reaction steps which decreases the yield of the product. In addition, the ozonolysis reaction which is difficult to handle and the expensive step d) which requires the use of triphenylphosphine makes this process uneconomic and unsuitable for a large-scale production.

The aim of the present invention is therefore to provide a novel process for the production of 9-dichloromethylene-1,2,3,4-tetrahydro-1,4-methano-naphthalen-5-ylamine that avoids the disadvantages of the known process and makes it possible to prepare 9-dichloromethylene-1,2,3,4-tetrahydro-1,4-methano-naphthalen-5-ylamine in high yields and good quality in an economically advantageous way with less reaction steps.

Thus, according to the present invention, there is provided a process for the preparation of 9-dichloromethylene-1,2,3,4-tetrahydro-1,4-methano-naphthalen-5-ylamine of formula I

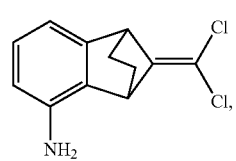

(I)

which process comprises
a) reacting cyclopentadiene with CXCl$_3$, wherein X is chloro or bromo; preferably bromo, in the presence of a radical initiator to a compound of formula II

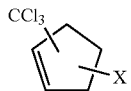
(II)

wherein X is chloro or bromo,
or aa) reacting cyclopentadiene with CXCl$_3$, wherein X is chloro, in the presence of a metal catalyst to a compound of formula II

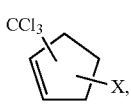
(II)

wherein X is chloro,
b) reacting the compound of formula II with a base in an appropriate solvent to the compound of formula III

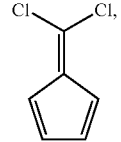
(III)

c) and converting the compound of formula III in the presence of 1,2-dehydro-6-nitrobenzene to the compound of formula IV

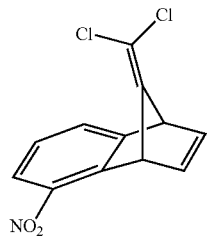
(IV)

and
d) hydrogenating the compound of formula IV with a hydrogen source in the presence of a metal catalyst.
One embodiment of this process comprises
a) reacting cyclopentadiene with CXCl$_3$, wherein X is chloro or bromo, in the presence of a radical initiator to a compound of formula II

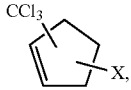
(II)

wherein X is chloro or bromo.

Reaction Step a) and aa):
The compound of formula II can occur in the following isomers or mixtures thereof:

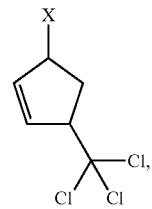
(IIa)

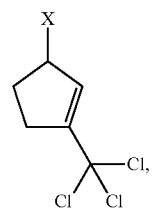
(IIb)

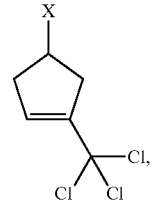
(IIc)

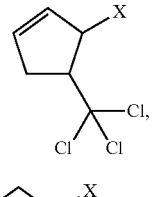
(IId)

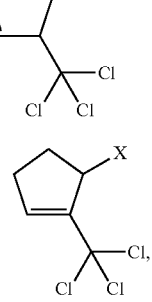
(IIe)
and

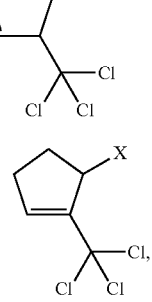
(IIf)

wherein X is chloro or bromo.

The product of reaction step a) and aa) can be used as it is for the following reaction step b). The isolation or purification of a specific isomer or a isomer mixture of formula II is not necessary. The compound of formula II and its isomers and the compound of formula IV are novel and especially developed for the process according to the invention and therefore constitute a further object of the invention.

In principle a large number of radical initiators of following classes can be applied for reaction step a): organic peroxides (for example methyl ethyl ketone peroxide, benzoyl peroxide), organic azo compounds, metal salts and complexes (Cu, Ru). Preferred radical initiators are selected from azobisisobutyronitrile, dibenzoylperoxide and bis(tert-butylcyclohexyl)peroxydicarbonate. Especially preferred is azobisisobutyronitrile.

Reaction step a) is advantageously performed at elevated temperatures, preferably at temperatures of from 20 to 100° C., preferably of from 60 to 100° C., most preferably of from 80 to 90° C. The use of bromotrichloromethane is preferred, especially under peroxide or azo compounds initiation.

In the especially preferred reaction step aa), cyclopentadiene is reacted with CCl$_4$ in the presence of a metal catalyst to a compound of formula II

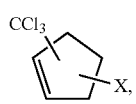

(II)

wherein X is chloro. For step aa), the presence of a radical initiator is not necessary, but can be of advantage to reduce catalyst loading (use of less catalyst).

Suitable metals for the catalysts are for example selected from ruthenium, copper, iron, palladium and rhodium. Preferred catalysts contain ruthenium (II) or copper (I) complexes. Especially preferred catalysts are selected from the group consisting of Ru(PPh$_3$)$_3$Cl$_2$, Ru(cumene)PPh$_3$Cl$_2$, Ru(Cp)PPh$_3$Cl$_2$, Grubbs I (benzylidene-bis(tricyclohexylphosphine)-dichlororuthenium) and CuCl in combination with an amine-ligand, especially a diamine or triamine ligand. Grubbs I, CuCl/tetramethylethylenediamine (TMEDA) or pentamethyldiethylentriamine are the most preferred catalysts.

Reaction step aa) can be performed in the presence of an inert solvent, preferably without a solvent when a Ru-catalyst is used. Reaction step aa) is advantageously performed at elevated temperatures, in particular at temperatures of from 20 to 100° C., preferably of from 60 to 100° C., most preferably of from 60° to 80° C. The product of reaction step aa) is a mixture of the 3 possible isomers. The isolation or purification of a specific isomer or a isomer mixture is not necessary.

A preferred embodiment of reaction step aa) can be efficiently performed by heating a mixture of cyclopentadiene with 1.5 to 3, in particular 2 equivalents of carbon tetrachloride in acetonitrile in the presence of 0.5 to 2 mol %, in particular 1 mol % copper I catalyst, preferably CuCl and 1 to 4 mol %, in particular 2 mol % tetramethylethane-1,2-diamine (TMEDA) to give 70-80% isolated yields of product after distillation.

Adding of a catalytic amount (usually 1 mol %) of a radical initiator as mentioned above, especially N,N-azobisisobutyronitril to the reaction mixture can reduce catalyst loading (use of less catalyst).

Reaction step aa) has further advantages. The use of 0014 is less expensive, the addition product with carbon tetrachloride (CTCM-cyclopentene) is much more stable than the bromo derivate (BTCM-cyclopentene), the reaction is much less exothermic and therefore more suitable for large scale production and no bromide anion is generated on the next step.

In reaction step a) and aa), CCl$_3$Br or 0014 is used in excess to cyclopentadiene, preferably 1.5-5 equivalents, in particular 2-3 equivalents of CCl$_3$Br or CCl$_4$ for one equivalent cyclopentadiene.

Reaction Step b):

Preferred bases for reaction step b) are alkali metal alcoholates, for example sodium tert-butoxide and potassium tert-butoxide or metal amides like NaNH$_2$ or lithiumdiisopropylamide. Except for ketones and esters, all inert solvents can be used. Appropriate solvents for reaction step b) are selected from methyl-tert-butylether (MTBE), methylcyclohexane (MCH) or a mixture thereof, tetrahydrofurane (THF), dyglime and toluene.

A further appropriate solvent for reaction step b) is chlorobenzene.

Reaction step b) is advantageously performed at a temperature range of −20 to +20° C., preferably at temperatures of from −10° C. to 10° C., most preferably of from −5° C. to 5° C. In a preferred embodiment of the present invention the compound of formula III (its solution) is used without isolation directly for the next reaction step. The compound of formula III is a valuable intermediate for the preparation of the compound of formula I. The compound of formula III is known from (a) Moberg, C.; Nilsson, M. *J. Organomet. Chem.* 1973, 49, 243-248. (b) Siemionko, R. K.; Berson, J. A. *J. Am. Chem. Soc.* 1980, 102, 3870-3882. However, the preparation method described in said reference is very unfavourable since: 1) The method could not be reproduced as described (low yield was obtained). 2) Utilizes very expensive pyrophoric and toxic starting material (nickelocene). 3) Produces large amount of metal-waste (nickel containing compounds). 4) The method cannot be scaled up for industrial use (unavailability of nickelocen in large amounts, dangerous handling of large quantities of nickelocen).

In contrast thereto, the preparation of the compound of formula III starting from cyclopentadiene is a novel and very efficient method and therefore constitutes a further object of the present invention.

Therefore, a further object of the present invention is a process for the preparation of the compound of formula III

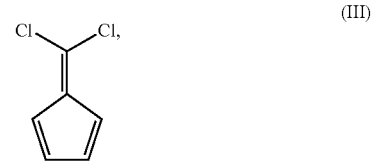

(III)

which process comprises a) reacting cyclopentadiene in the presence of a radical initiator and CXCl$_3$, wherein X is chloro or bromo, preferably bromo, to a compound of formula II

(II)

wherein X is chloro or bromo, and b) reacting the compound of formula II with a base in the presence of an appropriate solvent.

Reaction Step c)

1,2-dehydro-6-nitrobenzene is generated in situ [for example, starting from a 6-nitroanthranilic acid of formula (A),

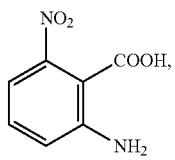

as described by L. Paquette et al, *J. Amer. Chem. Soc.* 99, 3734 (1977) and H. Seidel, Chemische Berichte, 34, 4351 (1901).

Reaction step c) is performed at elevated temperatures, preferably at temperatures of from 30° C. to 60° C., most preferably of from 30 to 40° C.

Reaction Step d)

Preferred metal catalysts for the hydrogenation reaction are selected from the group consisting of Raney nickel, platinum, preferably platinum on a carrier like carbon, palladium, preferably palladium on a carrier like carbon but are not limited to said group. An especially preferred catalyst is Raney nickel. Suitable hydrogen sources are hydrogen or hydrazine, preferably hydrogen.

Reaction step d) is performed at low to elevated temperatures, preferably at temperatures of from 0 to 80° C., preferably of from 30 to 60° C.

A preferred variant of the process according to the invention, comprises aa) reacting cyclopentadiene with $CXCl_3$, wherein X is chloro, in the presence of a metal catalyst wherein the metal component of the catalyst is selected from ruthenium, copper, iron, palladium and rhodium, to a compound of formula II

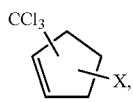

wherein X is chloro, b) reacting the compound of formula II with a base selected from alkali metal alcoholates in the presence of an appropriate solvent to the compound of formula III

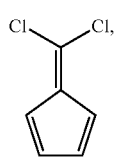

c) and converting the compound of formula III in the presence of 1,2-dehydro-6-nitrobenzene to the compound of formula IV

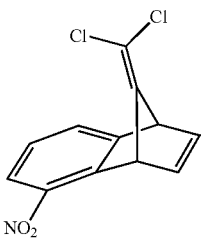

and d) hydrogenating the compound of formula IV with a hydrogen source in the presence of a metal catalyst.

PREPARATORY EXAMPLES

Example P1: Preparation of the Compound of Formula IIa

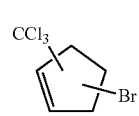

Azobisisobutyronitrile (2.5 g) was dissolved in bromotrichloromethane (250 g). Bromotrichloromethane (650 g) was loaded into a glass reactor under inert atmosphere (nitrogen) and heated to 85° C. ⅓ of the azobisisobutyronitrile solution (84 g) was added into the reactor at once and the reactor content was heated again to 85° C. followed by simultaneous addition of the remaining ⅔ of azobisisobutyronitrile solution (168.5 g) and a mixture of cyclopentadiene (100 g, freshly distilled) and methylcyclohexane (10 g) during 2.5 hours at 85° C. The reaction mixture was stirred for an additional 1 hour at 85° C., and then cooled to ambient temperature. Large amount of solvent (bromotrichloromethane) was evaporated in vacuum (60→70° C., 150→50 mbar). Methylcyclohexane (50 g) was added to the distillation residue and the distillation was continued (60→70° C., 150→15 mbar). The crude product (distillation residue) was dried in vacuum for an additional 30 min (70° C., 15 mbar). Yield 389 g of the compound of formula IIa in form of a brown oil, 94% pure, 92% yield, mixture of regioisomers.

Example P2: Preparation of the Compound of Formula III

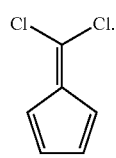

A glass reactor was loaded with bromo(trichloromethyl)cyclopentene (27.83 g, compound IIa), methylcyclohexane (62 mL), methyl-tert-butylether (62 mL) and bis(2-methoxyethyl) ether (diglyme, 6.7 g) under inert atmosphere (nitrogen). The mixture was cooled to −10° C. in an ice/NaCl bath. Sodium tert-butoxide (20.3 g) was added into the reactor as solid during 10 min while keeping the temperature below +5° C. When the addition was done, the reaction mixture was stirred at 0-5° C. for 2 hours. The reaction mixture was quenched with a mixture of ice-cold water (80 mL) and ice (40 g) and then the pH value of the water phase was adjusted to with 32% HCl (ca. 3 mL). The water phase was separated and the organic phase was dried over anhydrous potassium carbonate at 0° C. The potassium carbonate was filtered off and rinsed with methyl-tert-butylether (10 mL). Methyl ethyl ketone (10 g) was added to the combined filtrate as internal standard and the concentration of 6,6-dichlorofulvene (compound of formula III) was determined by $^1$H NMR spectroscopy. Yield 81% [9.7 g of 9.9% (ca. 0.53 M) solution]. The solution was stored in a freezer and then used for the next step.

Example P3: Preparation of the Compound of Formula IV

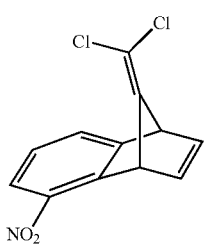

(IV)

A cold solution of 6,6-dichlorofulvene obtained in the previous step (9% in methyl-tert-butylether/methylcyclohexane=1:1) was placed in a glass reactor and heated quickly to 35° C. tert-pentyl nitrite (2.66 g) was added into the reactor followed by simultaneous addition of tert-pentyl nitrite (9.46 g) and a solution of 6-nitroanthranilic acid (11.6 g, 96.6%) in methyl ethyl ketone (42 mL) during 80 minutes at a temperature of 35° C. The reaction mixture was stirred for additional 30 min at the same temperature and then all the volatiles were removed by rotary evaporation. The remaining residue was crystallized from methanol (20 mL) at +5° C. for 15 hours. The brown crystalline material was filtered, washed with cold methanol (15 mL) and dried in air. Yield 7.10 g (42%, 98% pure product).

Example P4: Hydrogenation of the Compound of Formula IV

An autoclave was charged with THF (130 ml), wet Raney-Nickel (2 g) and compound of formula IV (20 g). The autoclave was closed, the content started to agitate, purged three times with nitrogen to remove oxygen and then three times with hydrogen. The reactor was pressurized with hydrogen to 5 bar. Then the content of the autoclave was heated to 40° C., maintaining pressure with additional hydrogen as needed. When hydrogen uptake stopped, typically after 3-4 h, the reaction mass was held another 30 min at 40° C. After this time, the pressure was released and the content was cooled to ambient temperature. The solvent was removed under vacuum and the resulting oil crystallized upon standing to yield 18 g of the yellowish to brownish compound of formula I (96%, 94% pure product).

Example P5: Preparation of CTCM-Cyclopentene of Formula IIa Using Grubbs-I Catalyst

(IIa)

A mixture of cyclopentadiene (2.0 g), azobisisobutyronitrile (0.5 g), benzylidene-bis(tricyclohexylphosphine)dichlororuthenium (Grubbs' 1$^{st}$ Generation Catalyst, 12.2 mg, 0.05 mol %) and carbon tetrachloride (14 g) was heated at 75° C. under inert atmosphere (argon). The conversion was monitored by GC. After 4 hours the reaction was completed to produce chloro(trichloromethyl)cyclopentene as a mixture of three isomers in 85% yield (GC, dodecane was used as a standard).

Example P6: Preparation of CTCM-Cyclopentene of Formula IIa Using CuCl/TMEDA Catalyst

(IIa)

Catalyst Solution:
A mixture of copper (I) chloride (0.99 g), tetramethylethylenediamine (TMEDA, 2.32 g) and acetonitrile (100 mL) was heated at 75° C. for 25 min under nitrogen atmosphere and then cooled to room temperature.
Cyclopentadiene Solution:
Freshly prepared cyclopentadiene (66.0 g) was dissolved in carbon tetrachloride (307 g).
Reaction:
Under nitrogen atmosphere acetonitrile (80 g) and 40% of the catalyst solution were placed into a glass reactor under nitrogen. The mixture was heated to a temperature of 75° C. Then 40% of the cyclopentadiene solution was added into the reactor in one portion followed by simultaneous addition of the rests of the catalyst solution and the cyclopentadiene solution while keeping the temperature between 60 and 70° C. The cyclopentadiene solution was added in 1 hour and the catalyst solution in 1.5 hours. The reaction mixture was stirred for an additional 1 hour at 70° C., cooled to ambient temperature and filtered. The solvent was removed by rotary evaporation and the residue was fractionated by vacuum distillation (40-45° C., 0.1 mbar). Yield 170 g (75%, 97-98% purity), mixture of three regioisomers.

Example P7: Preparation of the Compound of Formula III

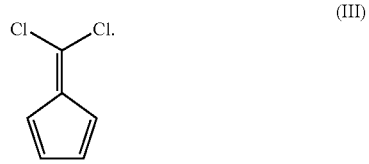

(III)

Sodium tert-butoxide (69.2 g) was stirred with chlorobenzene (175 ml) for 30 min at room temperature to produce a fine suspension.

A glass reactor was loaded with chloro(trichloromethyl) cyclopentene (69.1 g), chlorobenzene (275 ml), and bis(2-methoxyethyl) ether (diglyme, 21.1 g) under inert atmosphere (nitrogen). The mixture was cooled to −20° C. and the suspension of sodium tert-butoxide was added into the reactor portion-wise over 35 min while keeping the temperature below +3° C. When the addition was done, the reaction mixture was stirred at −5° C. for 3 hours. The reaction mixture was quenched with a mixture of 0.5 M aqueous HCl solution (300 ml) and ice (200 g). The pH value of the water phase was controlled to be pH 2. The water phase was separated and the organic phase was extracted with the same mixture of water and ice two times (This was necessary for a complete removal of tert-butanol and diglyme). The concentration of 6,6-dichlorofulvene was determined by $^1$H NMR spectroscopy using chlorobenzene (solvent) as an internal standard. Yield 75% [510 g of 6.8% (ca. 0.52 M) solution]. The solution was stored in a freezer or dry ice and then used for the next step.

Comment: The yield just after the quench (no further extractions) was 85%. The solution was lost in the phase separations.

A preferred benzonorbornene fungicide which can be advantageously prepared using the process according to the invention is 3-difluoromethyl-1-methyl-1H-pyrazole-4-carboxylic acid (9-dichloromethylene-1,2,3,4-tetrahydro-1,4-methano-naphthalen-5-yl)-amide of formula V

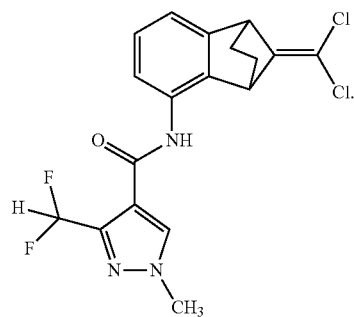

(V)

The compound of formula V is described, for example, in WO 2007/048556. The compound of formula V can occur in two enantiomeric forms. The compound of formula Va

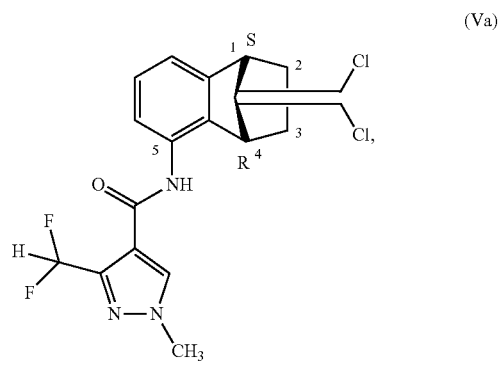

(Va)

which chemical designation is 3-difluoromethyl-1-methyl-1H-pyrazole-4-carboxylic acid ((1S,4R)-9-dichloromethylene-1,2,3,4-tetrahydro-1,4-methano-naphthalen-5-yl)-amide, and the compound of formula Vb

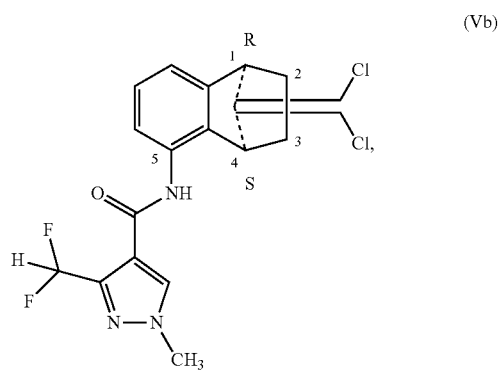

(Vb)

which chemical designation is 3-difluoromethyl-1-methyl-1H-pyrazole-4-carboxylic acid ((1R,4S)-9-dichloromethylene-1,2,3,4-tetrahydro-1,4-methano-naphthalen-5-yl)-amide. The optical rotation angles $[\alpha]^{23.5}$ are −119.26° and +119.23° (in tetrahydrofurane) respectively.

What is claimed is:
1. A compound of formula IV

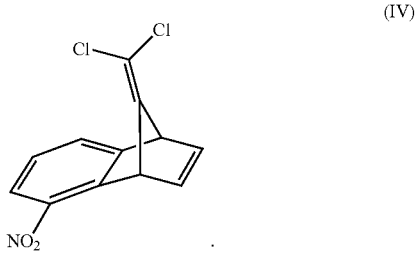 [SMILES: O=[N+]([O-])c1cccc2c1C1C=CC2C1=C(Cl)Cl]

(IV)

* * * * *